US00PP16767P2

(12) United States Plant Patent
Danziger

(10) Patent No.: US PP16,767 P2
(45) Date of Patent: Jul. 4, 2006

(54) ***GYPSOPHILA* PLANT NAMED 'DANGYPWHIFA'**

(50) Latin Name: *Gypsophila paniculata*
Varietal Denomination: Dangypwhifa

(75) Inventor: Gabriel Danziger, Moshav Nir-Zvi (IL)

(73) Assignee: Danziger "DAN" Flower Farm, Post Beit Dagan (IL)

( * ) Notice: Subject to any disclaimer, the term of this patent is extended or adjusted under 35 U.S.C. 154(b) by 34 days.

(21) Appl. No.: 11/036,337

(22) Filed: Jan. 18, 2005

(51) Int. Cl.
*A01H 5/00* (2006.01)

(52) U.S. Cl. ..... Plt./354

(58) Field of Classification Search ..... Plt./354
See application file for complete search history.

*Primary Examiner*—Kent Bell
*Assistant Examiner*—Louanne Krawczewicz Myers
(74) *Attorney, Agent, or Firm*—Foley & Lardner LLP

(57) ABSTRACT

A new and distinct *Gypsophila* plant named 'Dangypwhifa' characterized by having globular-shaped, double flowers, 10–11 mm in diameter; conic, bright white flowers arranged in clusters, creating a wide and impressive conic structure; 7–9 stems per plant in first flash; medium flash duration; erect, stable growth habit, branching from lower part of main stem, 80–90 cm in height; uniformly good quality of inflorescence year round; good post-production longevity, with vase life of 10–14 days; and commercially suitable product, marketed as a cut flower.

2 Drawing Sheets

Latin name of the genus and species of the claimed plant: *Gypsophila paniculata* (hybrid).
Variety denomination: 'Dangypwhifa'.

BACKGROUND OF THE INVENTION

The present invention relates to a new and distinct cultivar of *Gypsophila* plant, botanically known as *Gypsophila paniculata,* hereinafter referred to by the cultivar name 'Dangypwhifa'.

*Gypsophila,* of the Carophyllaceae family, consists of hardy annuals and perennials which are grown in various parts of the United States and Europe. *Gypsophila* plants are commonly called either Baby's Breath or Chalk Plant.

The new *Gypsophila* cultivar is a product of a planned breeding program conducted by the inventor, Gabriel Danziger, in Moshav Mishmar Hashiva, Israel. The objective of the breeding program is to develop a new *Gypsophila* variety with large, globular-shaped, double, bright white flowers; good vase life; and ease in harvesting variety.

The new *Gypsophila* cultivar was originated from a cross made in a controlled breeding program by the inventor in May of 2001, in Moshav Mishmar Hashiva, Israel. The female parent is the hybrid line designated 'CV.2088' (unpatented). The male parent is the hybrid line designated 'CV-184' (unpatented). The new *Gysophila* cultivar 'Dangypwhifa' was discovered and selected by the inventor, Gabriel Danziger, as a flowering plant within the progeny of the stated cross in a controlled environment in Moshav Mishmar Hashiva, Israel.

Asexual reproduction of the new cultivar by removing cutting from the initial plant was first performed in March of 2002 in Moshav Mishmar Hashiva, Israel, and has demonstrated that the combination of characteristics as herein disclosed for the new cultivar are firmly fixed and retained through successive generations of asexual reproduction. The instant plant reproduces true to type.

BRIEF DESCRIPTION OF THE INVENTION

The following traits have been repeatedly observed and are determined to be unique characteristics of 'Dangypwhifa' which in combination distinguish this *Gypsophila* as a new and distinct cultivar:

1) Globular-shaped, double flower, 10–11 mm in diameter;
2) Conic, bright white flowers arranged in clusters, creating a wide and impressive conic structure;
3) 7–9 stems per plant in first flash;
4) Medium flash duration;
5) Erect, stable growth habit, branching from lower part of main stem, 80–90 cm in height;
6) Uniformly good quality of inflorescence year round;
7) Good post-production longevity, with vase life of 10–14 days; and
8) Commercially suitable product, marketed as a cut flower.

Table 1 provides a comparison among plants of 'Dangypwhifa' and plants of the parents, 'CV-184' and 'CV.2088':

TABLE 1

| Trait | 'Dangypwhifa' | Female Parent 'CV.2088' | Male Parent 'CV-184' |
|---|---|---|---|
| Flower | Width: 9–12 mm<br>Color: bright white<br>Vaselife: 10–12 days | Width: 9–12 mm<br>Color: white<br>Vaselife: 10–12 days | Width: 9–12 mm<br>Color: white<br>Vaselife: 10–12 days |
| Inflorescence | Conic shape<br>900–1000 flowers per flowering stem | Conic shape<br>900–1000 flowers per flowering stem | Conic - open shape<br>900–1000 flowers per flowering stem |
| Yield (stems per plant in first flash) | 7–9 | 6–7 | 8–9 |

TABLE 1-continued

| Trait | 'Dangypwhifa' | Female Parent 'CV.2088' | Male Parent 'CV-184' |
|---|---|---|---|
| Growth Habit | Bush, branching from plant base Height: 80–90 cm | Bush, branching from plant base Height: 80–90 cm | Bush Height: 70–80 cm |
| Flowering time | Medium | Medium | Medium |

Of the many commercial cultivars known to the present inventor, the most similar in comparison to 'Dangypwhifa' is the *Gysophila* cultivar 'Danapurna' (unpatented). In side-by-side comparisons conducted in Moshav Mishmar Hashiva, Israel, plants of 'Dangywhifa' differed from plants of 'Danapurna' in the following characteristics provided in Table 2.

TABLE 2

| Characteristic | 'Dangypwhifa' | 'Danapurna' |
|---|---|---|
| Flower color | White group, RHS 155D | White group, RHS 155D |
| Inflorescence Formation | Conic | Flowers concentrate at upper part |
| Yield (stems per plant in first flash) | 7–9 | 10–12 |
| Stem height (cm) | 80–90 | 70–80 |
| Flowering time | 1 week less than 'Danapurna' | Medium |

BRIEF DESCRIPTION OF THE DRAWING

The accompanying photographic drawings illustrate the overall appearance of the new *Gypsophila* cultivar 'Dangypwhifa' showing the colors as true as is reasonably possible with colored reproductions of this type. Colors in the photographs may differ slightly from the color value cited in the detailed botanical description which accurately describe the color of 'Dangypwhifa'.

The first photograph shows a side view perspective of a flowering stem of 'Dangypwhifa'.

The second photograph shows a close-up view of a single flower of 'Dangypwhifa'.

DETAILED BOTANICAL DESCRIPTION

The new *Gypsophila* cultivar 'Dangypwhifa' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new *Gypsophila* cultivar as grown in a greenhouse in Moshav Mishmar Hashiva, Israel, under conditions which closely approximate those generally used in commercial practice.

Color references are made to The Royal Horticultural Society Colour Chart (R.H.S.), except where general colors of ordinary significance are used. Color values were taken under daylight conditions at approximately 12:00 p.m. in Moshav Mishmar Hashiva, Israel. The age of the plant described is 10 weeks.

Classification:
- *Botanical.*—Hybrid of *Gypsophila paniculata.*
- *Commercial.*—*Gypsophila* 'White Fire'.

Parentage:
- *Female parent.*—Hybrid line designated 'CV.2088' (unpatented).
- *Male parent.*—Hybrid line designated 'CV-184' (unpatented).

Origin: F1 hybrid.
Propagation: Stem cutting.
Plant:
General appearance and form:
- *Height.*—80–90 cm.
- *Width.*—50–60 cm.
- *Habit.*—Weak, apical dominance, branching from plant base.
- *Form.*—Upright bush type.

Flowering response: Long day.
Flowering season: Naturally during summer. All year with supplemental lighting.
Winter hardiness: Sensitive to temperatures below 9–10 C.
Lastingness of the individual bloom: 10–12 days.
Rooting: Use rooting hormone.
Foliage:
Overall shape of leaf: Lanceolate.
Base: Truncate.
Tip: Acuminate.
Margin: Entire.
Texture: Rough.
Main color of upper surface:
- *Mature leaf.*—Green, RHS 137 A.
- *Immature leaf.*—Green, RHS 137 A.

Main color of lower surface:
- *Mature leaf.*—Green, RHS 137 B.
- *Immature leaf.*—Green, RHS 137 B.

Venation color:
- *Upper surface.*—None.
- *Lower surface.*—None.

Size:
- *Length.*—9–10 cm.
- *Width.*—1.3–1.5 cm.

Stipules: None.
Petiole: None.
Inflorescence:
Natural flowering season: Long day.
Inflorescence size:
- *Length.*—40–60 cm.
- *Width.*—30–40 cm.

Fragrance: Typical to *Gypsophila.*
Corolla:
- *Form.*—Double flower.
- *Shape.*—Globular.
- *Average number.*—900–1000 flowers per flowering stem.
- *Depth.*—4–5 mm.
- *Diameter.*—10–11 mm.

Petal:
- *Petal number.*—45–50.
- *Petal shape.*—Overall: Spatulate with tip emarginated. Apex: Obtuse and Emarginate. Base: Acute.
- *Petal markings.*—None.
- *Length.*—4–6 mm.
- *Width.*—1–2 mm.

*Margin.*—Entire.
*Margin color.*—White, RHS 155D.
*Petal color.*—Upper surface: White, RHS 155 D. Lower surface: White, RHS 155 D.

Sepal:
*Sepal number.*—5–6.
*Sepal shape.*—Elliptic.
*Apex.*—Obtuse.
*Base.*—Truncate.
*Length.*—3–4 mm.
*Width.*—1.5 mm.
*Margin.*—Both surfaces: Entire.
*Margin color.*—Transparent, white group, RHS 155 D.
*Sepal color.*—Upper surface: Green group, RHS 137 C. Lower surface: Green group, RHS 137 B.

Stem:
*Number per plant.*—7–9 in first flash.
*Average length.*—80–90 cm.
*Average diameter.*—5–6 mm.
*Internode length.*—4–6 cm.
*Color.*—Yellow-Green, RHS 144 B.
*Lateral branches.*—4–10.

Spur: None.

Bud:
*Response.*—Long day.
*Color.*—Yellow group, RHS 2 D.
*Size before opening.*—Height: 3 mm. Diameter: 4 mm.
*Shape.*—Oblate.

Pedicel:
*Pedicel length.*—8–10 mm.
*Pedicel color.*—Yellow-Green, RHS 146 A.

Peduncle:
*Appearance and angle.*—Thyrse, 35.
*Length.*—80–90 cm.
*Diameter.*—5–6 mm.
*Strength.*—Stable and moderately strong.
*Color.*—Yellow-Green, RHS 144B.

Reproductive organs:

Androecium:

Stamen:
*Number.*—5–10 (seldom seen).
*Color.*—White group, RHS 155D (transparent).

Anthers:
*Number.*—5–10 (seldom seen).
*Color.*—Orange-white group, RHS 159 D.

Pollen:
*Amount.*—A lot.
*Color.*—Orange-white group, RHS 159 D.

Gynoecium:

Pistil:
*Number.*—2.
*Shape.*—Convex.
*Color.*—White group, RHS 155 D (transparent).

Ovary:
*Color.*—Yellow-green group, RHS 144 D.

Seeds:
*Width.*—1 mm.
*Length.*—1 mm.
*Shape.*—Kidney-shaped.
*Texture.*—Canescent.
*Color.*—Brown group, RHS 200 A.

Fruit:
*Width.*—2–3 mm.
*Length.*—2–3 mm.
*Shape.*—Oblate with conical tip.
*Color.*—Greyed-yellow group, RHS 161 A.

Disease resistance: No information is currently available.

Disease susceptibility: No information is currently available.

I claim:

1. A new and distinct *Gypsophila* plant named ‘Dangypwhifa’, substantially as illustrated and described herein.

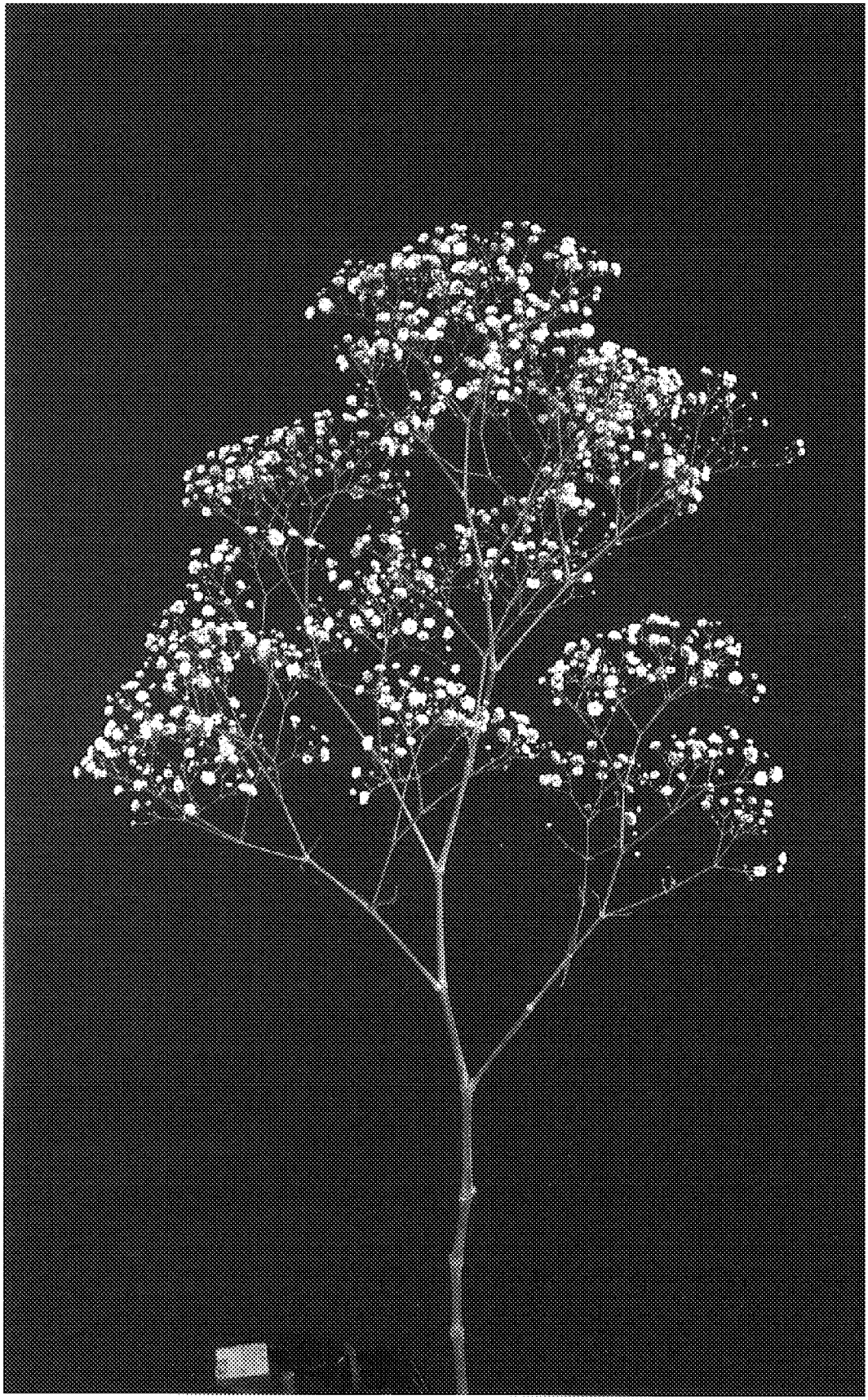

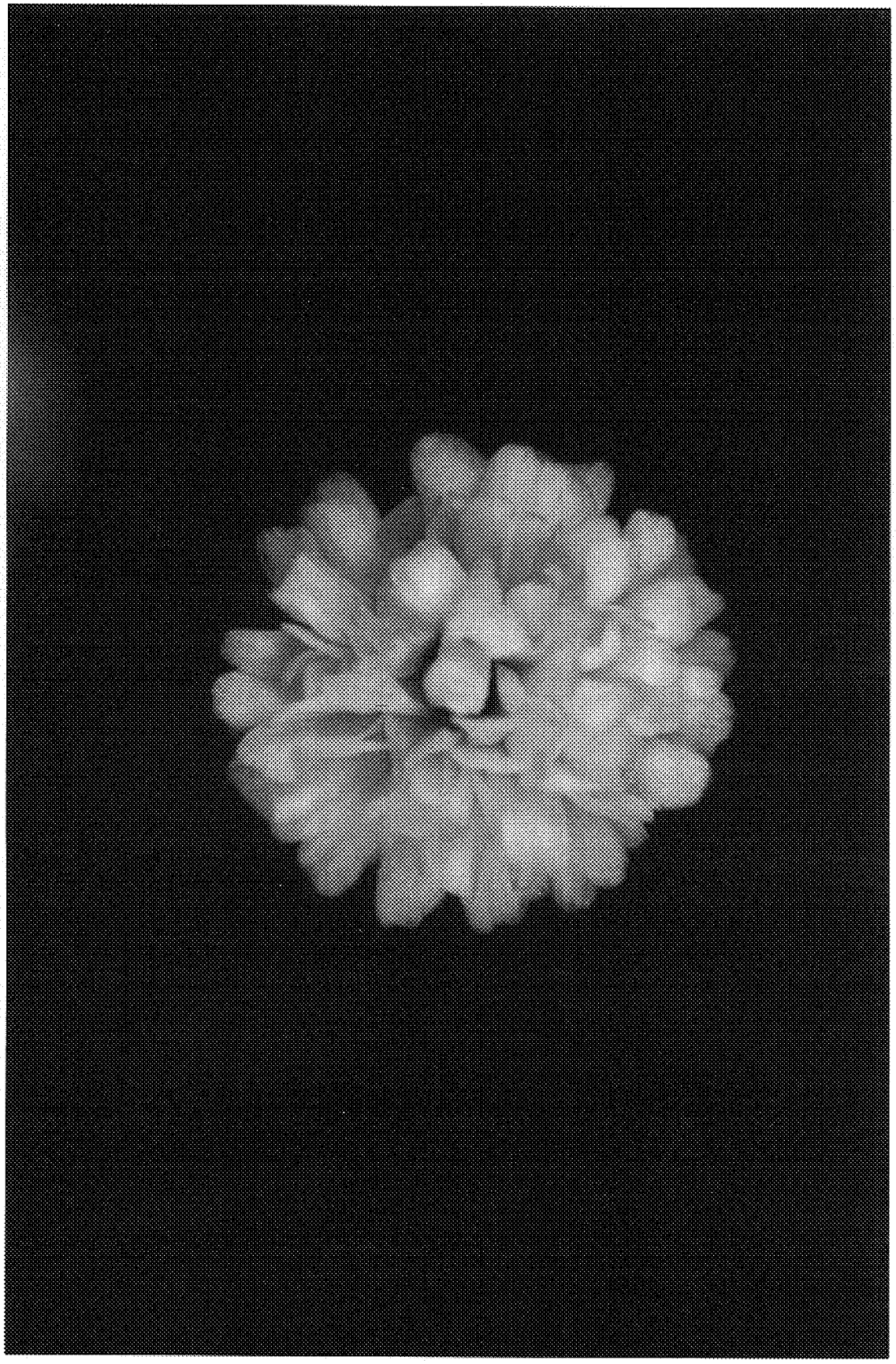

* * * * *